(12) United States Patent
Tsuyuki (10) Patent No.: US 11,241,212 B2
(45) Date of Patent: Feb. 8, 2022

(54) MEDICAL APPARATUS

(71) Applicant: CANON MEDICAL SYSTEMS CORPORATION, Otawara (JP)

(72) Inventor: Masaharu Tsuyuki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 154 days.

(21) Appl. No.: 16/807,587

(22) Filed: Mar. 3, 2020

(65) Prior Publication Data

US 2020/0281555 A1 Sep. 10, 2020

(30) Foreign Application Priority Data

Mar. 5, 2019 (JP) .............................. JP2019-039456

(51) Int. Cl.
*A61B 6/00* (2006.01)
*A61B 6/06* (2006.01)
*G06T 7/00* (2017.01)

(52) U.S. Cl.
CPC .............. *A61B 6/5282* (2013.01); *A61B 6/06* (2013.01); *G06T 7/0012* (2013.01); *G06T 2207/30012* (2013.01); *G06T 2211/40* (2013.01)

(58) Field of Classification Search
CPC ........... A61B 6/00; A61B 6/06; A61B 6/5282; A61B 6/03; A61B 6/4085; A61B 6/5205; A61B 6/4014; A61B 6/4035; A61B 6/4291; G06T 7/00; G06T 7/0012; G06T 2207/30012; G06T 2211/40; G06T 11/003; G06T 11/008
See application file for complete search history.

(56) References Cited

U.S. PATENT DOCUMENTS

| | | | |
|---|---|---|---|
| 10,559,101 B2 * | 2/2020 | Lee ........................ | G06T 11/008 |
| 2016/0095561 A1 | 4/2016 | Tamura | |
| 2020/0219252 A1 * | 7/2020 | Tsuyuki ................... | G06N 3/08 |
| 2021/0100521 A1 * | 4/2021 | Iwai ....................... | G01N 23/044 |

FOREIGN PATENT DOCUMENTS

JP 2016-67943 A 5/2016

* cited by examiner

*Primary Examiner* — Jurie Yun
(74) *Attorney, Agent, or Firm* — Oblon, McClelland, Maier & Neustadt, L.L.P.

(57) ABSTRACT

A medical apparatus of embodiments includes processing circuitry. The processing circuitry is configured to input third projection data to a first trained model to generate fourth projection data, the first trained model being generated through learning using first projection data collected by a first X-ray detector included in a first scanner and relatively greatly affected by scattered rays as learning data of an input side and using second projection data relatively less affected by scattered rays as learning data of an output side, the first trained model being configured to generate, on the basis of the third projection data collected by a second X-ray detector included in a second scanner, the fourth projection data in which the influence of scattered rays in the third projection data has been reduced. The first projection data is collected by the first X-ray detector in a case where a collimator provided in a first X-ray source included in the first scanner has a first opening width. The second projection data is collected by the first X-ray detector in a case where the collimator has an opening width smaller than the first opening width.

5 Claims, 11 Drawing Sheets

| TUBE VOLTAGE | RADIATION ANGLE | TRAINED MODEL |
|---|---|---|
| 80 [kV] | 337.5° ~22.5° | ○○ |
| | 22.5° ~45° | ○○ |
| | ⋮ | ⋮ |
| | 315° ~337.5° | ○○ |
| 120 [kV] | 337.5° ~22.5° | ○○ |
| | 22.5° ~45° | ○○ |
| | ⋮ | ⋮ |
| | 315° ~337.5° | ○○ |
| 135 [kV] | 337.5° ~22.5° | ○○ |
| | 22.5° ~45° | ○○ |
| | ⋮ | ⋮ |
| | 315° ~337.5° | ○○ |
| ... | ... | ... |

MODEL FOR HEAD
MODEL FOR CHEST
MODEL FOR ABDOMEN

MEDICAL APPARATUS

CROSS-REFERENCE TO RELATED APPLICATION

The present application claims priority based on Japanese Patent Application No. 2019-039456, filed on Mar. 5, 2019, the content of which is incorporated herein by reference.

FIELD

Embodiments disclosed in the present description and drawings relate to a medical apparatus.

BACKGROUND

X-ray CT apparatuses which obtain tomographic images by radiating X rays to an examination subject and scanning the examination subject have been known. There is an X-ray CT apparatus which radiates X rays having an expanse (cone angle) in a body axis direction and includes a detector including elements arranged in the body axis direction and a channel direction. Particularly, this type of X-ray CT apparatus has a problem that the definition of CT images deteriorates due to the influence of scattered rays.

DETAILED DESCRIPTION

A medical apparatus of embodiments includes processing circuitry. The processing circuitry is configured to input third projection data to a first trained model to generate fourth projection data, the first trained model being generated through learning using first projection data collected by a first X-ray detector included in a first scanner and relatively greatly affected by scattered rays as learning data of an input side and using second projection data relatively less affected by scattered rays as learning data of an output side, the first trained model being configured to generate, on the basis of the third projection data collected by a second X-ray detector included in a second scanner, the fourth projection data in which the influence of scattered rays in the third projection data has been reduced, or the processing circuitry is configured to subtract, from the third projection data, scattered ray component data obtained by inputting the third projection data to a second trained model, to generate fifth projection data, the second trained model being generated through learning using the first projection data as learning data of an input side and using a difference between the first projection data and the second projection data as learning data of an output side, the second trained model being configured to generate, on the basis of the third projection data, the scattered ray component data obtained by extracting the influence of scattered rays in the third projection data. The first projection data is collected by the first X-ray detector in a case where a collimator provided in a first X-ray source included in the first scanner has a first opening width. The second projection data is collected by the first X-ray detector in a case where the collimator has an opening width smaller than the first opening width. Hereinafter, a medical apparatus of embodiments will be described with reference to the drawings.

First Embodiment

Figure 1:
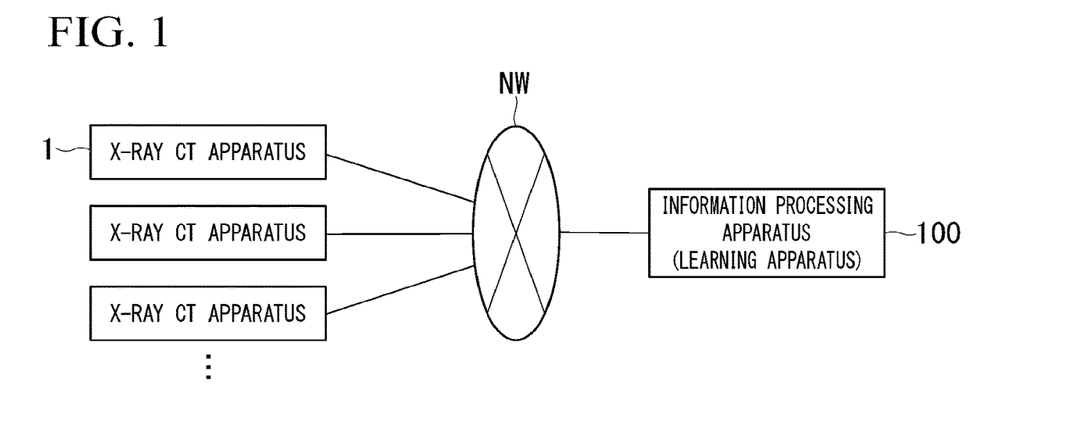
FIG. 1 is a configuration diagram of a medical diagnostic system including an X-ray CT apparatus using a medical apparatus.

FIG. 1 is a configuration diagram of a medical diagnostic system including an X-ray computed tomography (CT) apparatus 1 using a medical apparatus. As shown in the figure, one or more X-ray CT apparatuses 1 are connected to an information processing apparatus (learning apparatus) 100 through a network NW. The network NW may include a wide area network (WAN), a local area network (LAN), the Internet, and the like, for example. The information processing apparatus 100 generates a trained model on the basis of learning data collected from the X-ray CT apparatuses 1 and the like and provides the trained model to the X-ray CT apparatuses 1. Although the learning apparatus and the X-ray CT apparatus are separate in FIG. 1 and the following description, the X-ray CT apparatus may perform the same learning processing as that performed by the learning apparatus. That is, the learning apparatus may be included in the X-ray CT apparatus. Hereinafter, the X-ray CT apparatus 1 will be described first and then the information processing apparatus 100 will be described.

Figure 2:
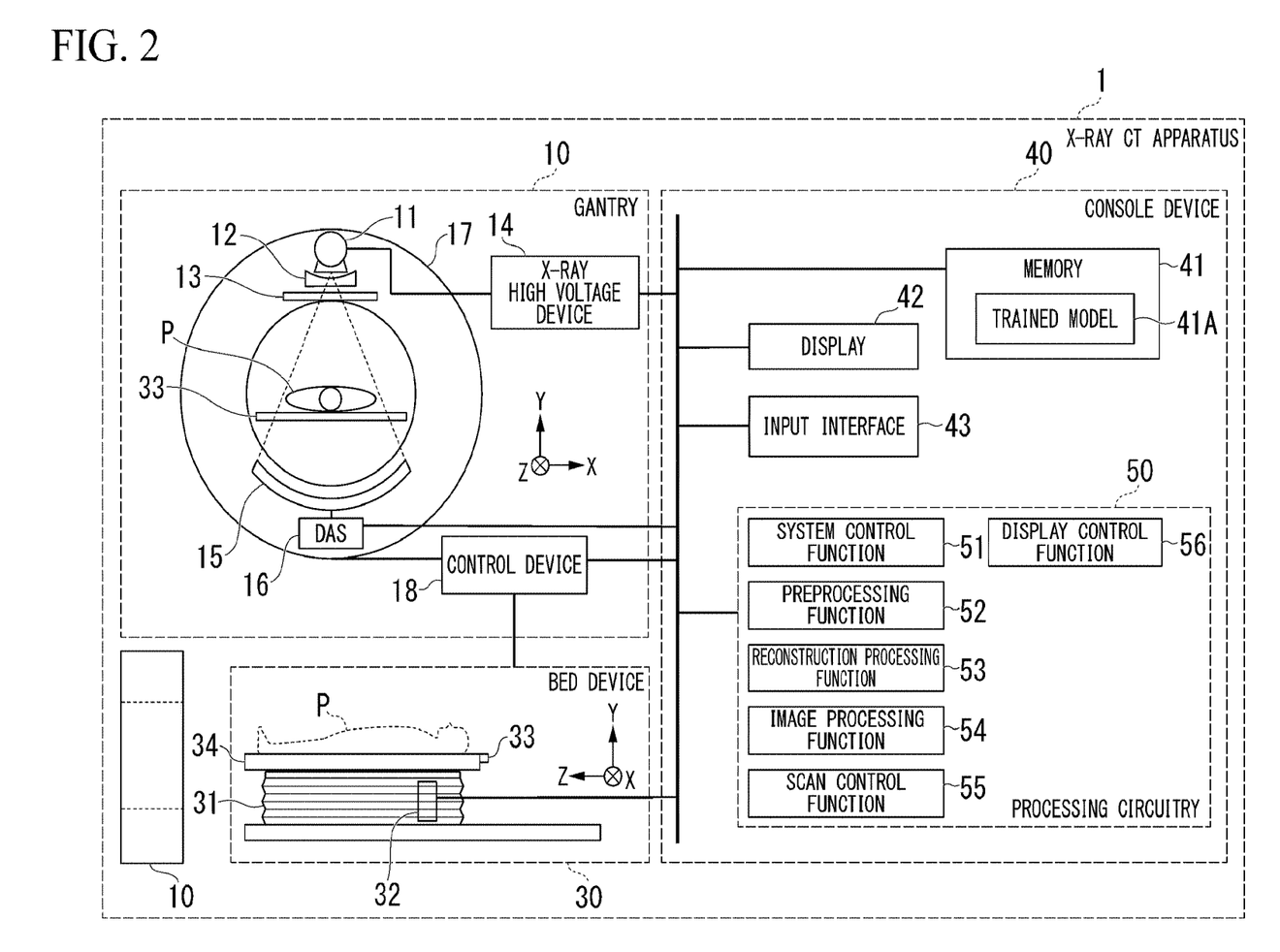
FIG. 2 is a configuration diagram of an X-ray CT apparatus according to an embodiment.

FIG. 2 is a configuration diagram of the X-ray CT apparatus 1 according to an embodiment. The X-ray CT apparatus 1 includes, for example, a gantry 10, a bed device 30, and a console device 40. Although FIG. 2 shows both a diagram of the gantry 10 viewed in a Z-axis direction and a diagram viewed in an X-axis direction for convenience of description, there is actually one gantry 10. In embodiments, a rotation axis of a rotary frame 17 in a non-tilted state or a longitudinal direction of a top board 33 of the bed device 30 is defined as a Z-axis direction, an axis at a right angle to the Z-axis direction that is parallel to the floor is defined as an X-axis direction, and a direction at a right angle to the Z-axis direction that is perpendicular to the floor is defined as a Y-axis direction.

The gantry 10 includes, for example, an X-ray tube 11, a wedge 12, a collimator 13, an X-ray high voltage device 14, an X-ray detector 15, a data collection system (hereinafter, data acquisition system (DAS) 16, the rotary frame 17 and a control device 18. A configuration including the X-ray tube 11, the wedge 12, the collimator 13, the X-ray high voltage device 14, the X-ray detector 15, the DAS 16 is an example of a "second scanner."

The X-ray tube 11 generates X rays by radiating thermions from a cathode (filament) to an anode (target) according to application of a high voltage from the X-ray high voltage device 14. The X-ray tube 11 includes a vacuum tube. For example, the X-ray tube 11 may be a rotating anode type X-ray tube which generates X rays by radiating thermions to a rotating anode. The X-ray tube 11 is an example of a "second X-ray source."

The wedge 12 is a filter for controlling the amount of X rays radiated from the X-ray tube 11 to an examination subject P. The wedge 12 attenuates X rays transmitted through the wedge 12 such that a distribution of the amount of X rays radiated from the X-ray tube 11 to the examination subject P becomes a predetermined distribution. The wedge 12 is also called a wedge filter or a bow-tie filter. For example, the wedge 12 may be manufactured by processing aluminum such that it has a predetermined target angle and a predetermined thickness.

The collimator 13 is a mechanism for narrowing a radiation range of X rays that have been transmitted through the wedge 12. The collimator 13 narrows a radiation range of X rays, for example, by forming a slit according to combination of a plurality of lead plates. The collimator 13 may also be called an X-ray aperture. Narrowing a range of the collimator 13 may be mechanically driven.

The X-ray high voltage device 14 includes, for example, a high voltage generation device and an X-ray control device. The high voltage generation device has an electrical circuit including a transformer (trans), a rectifier and the like and generates a high voltage to be applied to the X-ray tube 11. The X-ray control device controls an output voltage of the high voltage generation device in response to the amount of X rays generated by the X-ray tube 11. The high voltage generation device may perform voltage boosting through the aforementioned transformer or perform voltage boosting through an inverter. The X-ray high voltage device 14 may be provided in the rotary frame 17 or provided on the side of a fixed frame (not shown) of the gantry 10.

The X-ray detector 15 detects the intensity of X rays that have been generated by the X-ray tube 11, passed through the examination subject P and applied to the X-ray detector 15. The X-ray detector 15 is an example of a "second X-ray detector." The X-ray detector 15 outputs an electrical signal (an optical signal or the like is possible) in response to the detected intensity of X rays to the DAS 18. The X-ray detector 15 includes, for example, a plurality of X-ray detection element strings. The plurality of X-ray detection element strings are obtained by arranging a plurality of X-ray detection elements in a channel direction along an arc having the focus of the X-ray tube 11 as a center. The plurality of X-ray detection element strings are arranged in a slice direction (row direction).

The X-ray detector 15 is, for example, an indirect detector including a grid, a scintillator array and an optical sensor array. The scintillator array includes a plurality of scintillators. Each scintillator has scintillator crystals. Scintillator crystals emit an amount of light in response to the intensity of input X rays. The grid is disposed on a surface of the scintillator array to which X rays are input and includes an X-ray shielding plate having a function of absorbing scattered X rays. Meanwhile, there is a case in which the grid is called a collimator (one-dimensional collimator or two-dimensional collimator). The optical sensor array includes, for example, optical sensors such as photomultipliers (PMTs). The optical sensor array outputs an electrical signal in response to the amount of light emitted from the scintillators. The X-ray detector 15 may be a direct conversion type detector including a semiconductor element which converts input X rays into an electrical signal.

The DAS 16 includes, for example, an amplifier, an integrator, and an A/D converter. The amplifier performs amplification processing on an electrical signal output from each X-ray detection element of the X-ray detector 15. The integrator integrates amplified electrical signals over a view period (which will be described later). The A/D converter converts an electrical signal representing an integration result into a digital signal. The DAS 16 outputs detection data based on the digital signal to the console device 40. The detection data is a digital value of an X-ray intensity identified through a channel number and a string number of an X-ray detection element that is a generation source, and a view number indicating a collected view. A view number is a number that varies according to rotation of the rotary frame 17 and is, for example, a number that increases according to rotation of the rotary frame 17. Accordingly, a view number is information representing a rotation angle of the X-ray tube 11. A view period is a period from a rotation angle corresponding to a certain view number to a rotation angle corresponding to the next view number. The DAS 16 may detect view switching through a timing signal input from the control device 18, an internal timer or a signal acquired from a sensor which is not shown. When X rays are continuously emitted by the X-ray tube 11 during full scanning, the DAS 16 collects detection data groups corresponding to the entire circumference (360 degrees). When X rays are continuously emitted by the X-ray tube 11 during half scanning, the DAS 16 collects detection data corresponding to half a circumference (180 degrees).

The rotary frame 17 is an annular member which supports the X-ray tube 11, the wedge 12, the collimator 13 and the X-ray detector 15 such that the X-ray tube 11, the wedge 12 and the collimator 13 face the X-ray detector 15. The rotary frame 17 is rotatably supported by a fixed frame having the examination subject P introduced thereinto as a center. The rotary frame 17 additionally supports the DAS 16. Detection data output from the DAS 16 is transmitted from a transmitter having a light emitting diode (LED) provided in the rotary frame 17 to a receiver having a photodiode provided in a non-rotary part (e.g., a fixed frame) of the gantry 10 through optical communication and forwarded to the console device 40 through the receiver.

Meanwhile, a method of transmitting detection data from the rotary frame 17 to a non-rotary part is not limited to the aforementioned method using optical communication and any non-contact type transmission method may be employed. The rotary frame 17 is not limited to an annular member and may be a member such as an arm as long as it can support and rotate the X-ray tube 11 and the like.

Although the X-ray CT apparatus 1 may be, for example, a Rotate/Rotate-Type X-ray CT apparatus (third-generation CT) in which both the X-ray tube 11 and the X-ray detector 15 are supported by the rotary frame 17 and rotate around the examination subject P, it is not limited thereto and may be a Stationary/Rotate-Type X-ray CT apparatus (fourth-generation CT) in which a plurality of X-ray detection elements arranged in an annular shape are fixed to a fixed frame and the X-ray tube 11 rotates around the examination subject P.

The control device 18 includes, for example, processing circuitry having a processor such as a central processing unit (CPU) and a driving mechanism including a motor, an actuator and the like. The control device 18 receives an input signal from an input interface 43 attached to the console device 40 or the gantry 10 and controls operations of the gantry 10 and the bed device 30. For example, the control device 18 may rotate the rotary frame 17, tilt the gantry 10 or move the top board 33 of the bed device 30. When the control device 18 tilts the gantry 10, the control device 18 rotates the rotary frame 17 on an axis parallel to the Z-axis direction on the basis of an inclination angle (tilt angle) input to the input interface 43. The control device 18 ascertains a rotation angle of the rotary frame 17 through an output of a sensor which is not shown, and the like. In addition, the control device 18 provides the rotation angle of the rotary frame 17 to a scan control function 55 at any time. The control device 18 may be provided in the gantry 10 or provided in the console device 40.

The bed device 30 mounts and moves the examination subject P to be scanned and introduces the examination subject P into the rotary frame 17 of the gantry 10. The bed device 30 includes, for example, a base 31, a bed driving device 32, the top board 33, and a supporting frame 34. The base 31 includes a housing which supports the supporting frame 34 such that the supporting frame 34 can move in a vertical direction (Y-axis direction). The bed driving device 32 includes a motor and an actuator. The bed driving device 32 moves the top board 33 on which the examination subject P is mounted in the longitudinal direction (Z-axis direction) of the top board 33 along the supporting frame 34. The top board 33 is a plate-shaped member on which the examination subject P is mounted.

The bed driving device 32 may move the supporting frame 34 in the longitudinal direction of the top board 33 as well as the top board 33. Further, contrary to the above, the gantry 10 may be movable in the Z-axis direction and the rotary frame 17 may be controlled such that it comes near the examination subject P in accordance with movement of the gantry 10. In addition, both the gantry 10 and the top board 33 may be configured such that they are movable. Furthermore, the X-ray CT apparatus 1 may be a type of apparatus in which the examination subject P is scanned in a lying position or a sitting position. In this case, the X-ray CT apparatus 1 has an examination subject supporting function instead of the bed device 30 and the gantry 10 rotates the rotary frame 17 in an axial direction perpendicular to the floor.

The console device 40 includes, for example, a memory 41, a display 42, the input interface 43, and processing circuitry 50. Although the console device 40 is described as a body separate from the gantry 10 in embodiments, some or all components of the console device 40 may be included in the gantry 10. The console device 40 in the present embodiment is an example of a "medical apparatus."

The memory 41 is realized, for example, by a semiconductor element such as a random access memory (RAM) or a flash memory, a hard disk, an optical disc, or the like. The memory 41 stores, for example, detection data, projection data, reconstructed images, CT images, and the like. Such data may be stored in an external memory with which the X-ray CT apparatus 1 can communicate instead of the memory 41 (or in addition to the memory 41). For example, the external memory may be controlled through a cloud server which manages the external memory by receiving a read request.

The display 42 displays various types of information. For example, the display 42 displays medical images (CT images) generated by processing circuitry, a graphical user interface (GUI) image through which various operations from an operator are received, and the like. For example, the display 42 may be a liquid crystal display, a cathode ray tube (CRT), an organic electroluminescence (EL) display, or the like. The display 42 may be provided in the gantry 10. The display 42 may be a desktop type or a display device (e.g., a tablet terminal) which can wirelessly communicate with the main body of the console device 40.

The input interface 43 receives various input operations from an operator and outputs electrical signals representing details of received input operations to the processing circuitry 50. For example, the input interface 43 may receive operations of inputting collection conditions when detection data or projection data (which will be described later) is collected, reconstruction conditions when a CT image is reconstructed, image processing conditions when a postprocessing image is generated from a CT image, and the like. For example, the input interface 43 may be realized by a mouse, a keyboard, a touch panel, a trackball, a switch, a button, a joystick, a camera, an infrared sensor, a microphone, or the like. The input interface 43 may be provided in the gantry 10. In addition, the input interface 43 may be realized by a display device (e.g., a tablet terminal) which can wirelessly communicate with the main body of the console device 40.

The processing circuitry 50 controls the overall operation of the X-ray CT apparatus 1. The processing circuitry 50 executes, for example, a system control function 51, a preprocessing function 52, a reconstruction processing function 53, an image processing function 54, the scan control function 55, a display control function 56, and the like. For example, these functions may be realized by a hardware processor such as a central processing unit (CPU) executing a program (software). Some or all of these components may be realized by hardware (circuit; including a circuitry) such as a large scale integration (LSI) circuit, an application specific integrated circuit (ASIC), a field-programmable gate array (FPGA), or a graphics processing unit (GPU) or realized by software and hardware in cooperation. A program may be stored in a non-transitory storage device such as a memory 41 in advance or stored in a detachable non-transitory storage medium such as a DVD or a CD-ROM and installed by inserting the storage medium into a drive device.

Components included in the console device 40 or the processing circuitry 50 may be distributed and realized by a plurality of hardware circuits. The processing circuitry 50 may be realized by a processing device which can communicate with the console device 40 instead of being included in the console device 40. For example, the processing device may be a workstation connected to a single X-ray CT apparatus or a device (e.g., a cloud server) which is connected to a plurality of X-ray CT apparatuses and integrally executes processes equivalent to those of the processing circuitry 50 which will be described below.

The system control function 51 controls various functions of the processing circuitry 50 on the basis of input operations received through the input interface 43. The preprocessing function 52 performs preprocessing such as logarithmic conversion processing, offset correction processing, interchannel sensitivity correction processing and beam hardening correction on detection data output from the DAS 16 and generates projection data.

Further, the preprocessing function 52 generates projection data after scattered ray correction (an example of fourth projection data) by inputting projection data (an example of third projection data) generated as above to a trained model 41A stored in the memory 41. The preprocessing function 52 stores the generated projection data after scattered ray correction in the memory 41. For example, information that identifies a view representing a radiation angle is assigned to projection data. Alternatively, the preprocessing function 52 may generate detection data after scattered ray correction by inputting detection data output from the DAS 16 to the trained model 41A. Details and learning processing of the trained model 41A will be described later.

The reconstruction processing function 53 performs reconstruction processing through a filter correction reverse projection method, a sequential approximation reconstruction method or the like on projection data generated by the preprocessing function 52 to generate a CT image and stores the generated CT image in the memory 41.

The image processing function 54 converts CT image data into three-dimensional image or section image data with an arbitrary section through a known method on the basis of an input operation received by the input interface 43. Conversion into three-dimensional image data may be performed by the preprocessing function 52.

The scan control function 55 instructs the X-ray high voltage device 14, the DAS 16, the control device 18 and the bed driving device 32 to control detection data collection processing in the gantry 10. The scan control function 55 controls operation of each component when imaging for collecting positioning images and capturing of images used for diagnosis are performed.

According to the above-described configuration, the X-ray CT apparatus 1 scans the examination subject P in a scan mode such as helical scan, conventional scan or step-and-shot. The helical scan is a mode of rotating the rotary frame 17 while moving the top board 33 to scan the examination subject P in a spiral form. The conventional scan is a mode of rotating the rotary frame 17 in a state in which the top board 33 is stopped to scan the examination subject P in a circular orbit. The step-and-shot is a mode of moving the position of the top board 33 at specific intervals to perform the conventional scan in a plurality of scan areas.

[Learning Processing]

Figure 3:
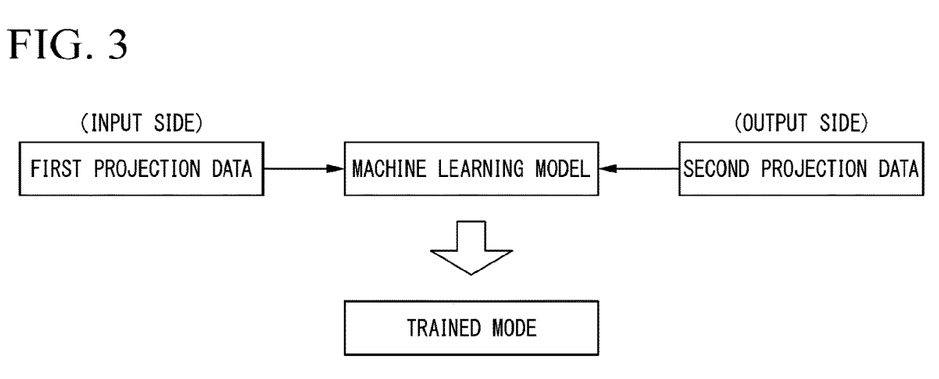
FIG. 3 is a diagram showing an overview of learning processing.

Hereinafter, trained model generation processing (learning processing) performed by the information processing apparatus 100 will be described. FIG. 3 is a diagram showing an overview of learning processing. The information processing apparatus 100 performs machine learning using a group of a plurality of sets of first projection data and second projection data which are collected by the first scanner for a machine learning model for which nodes and a combination relation have been set in advance and parameters (combination coefficients and weights) as initial values have been set. The first scanner includes an X-ray tube, a wedge, a collimator, an X-ray high voltage device, an X-ray detector, and a DAS included in an arbitrary X-ray CT apparatus. The information processing apparatus 100 adjusts the parameters through a method such as back propagation using the first projection data as learning data of an input side and using the second projection data as learning data of an output side (training data, correct answer data) of an input side. Although the machine learning model is a deep neural network (DNN) using a convolution neural network (CNN), for example, the present invention is not limited thereto and any model may be used. When the information processing apparatus 100 performs back propagation on a group of a predetermined number of sets of first projection data and second projection data, the information processing apparatus 100 ends the processing. The machine learning model at the time becomes a trained model.

The first projection data is projection data collected in the first scanner in an arbitrary state. The second projection data is projection data collected in the first scanner and less affected by scattered rays than the first projection data. In the present embodiment, the second projection data is projection data collected by limiting an X-ray radiation range to be less than that for the first projection data and increasing the number of radiations to that extent.

Figure 4:
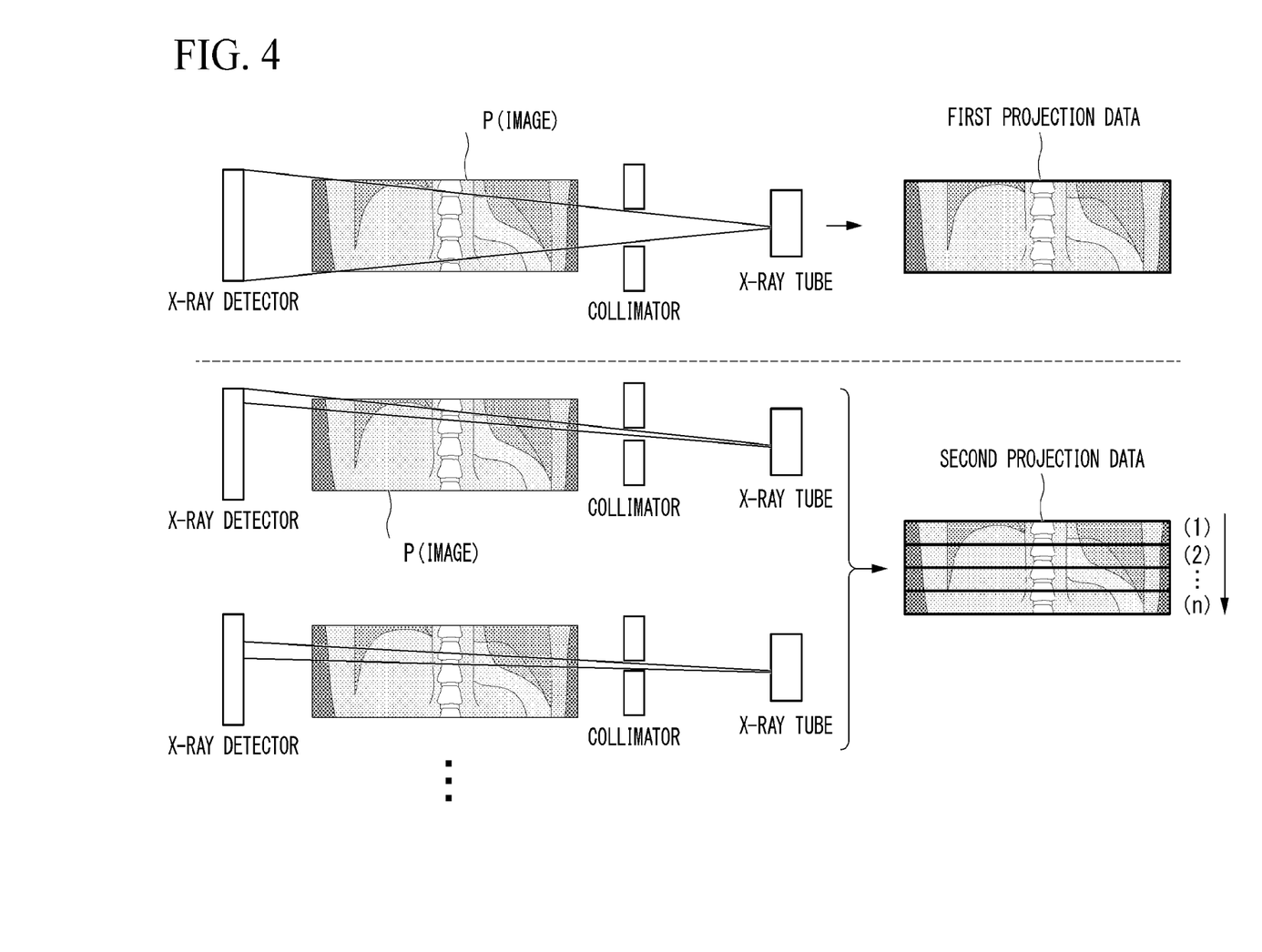
FIG. 4 is a diagram for describing first projection data and second projection data in a first embodiment.

FIG. 4 is a diagram for describing the first projection data and the second projection data in the first embodiment. As shown in the figure, the first projection data is projection data collected by setting an opening width of a collimator on the side of an X-ray tube to be relatively wide (setting a relatively wide cone angle) while rotating the X-ray tube once, for example. On the other hand, the second projection data is projection data collected by rotating the X-ray tube n times (n is a natural number equal to or greater than 2) while setting the opening width of the collimator on the side of the X-ray tube to be relatively narrow (reducing the cone angle by decreasing the opening width in the Z direction (refer to FIG. 2)) and changing a radiation angle by changing the opening position of the collimator. Although images in which a scan target is a human body are represented in the figure, a phantom and the like may be used as a scan target. It is desirable to acquire the first projection data and the second projection data by scanning the same scan target.

Figure 5:
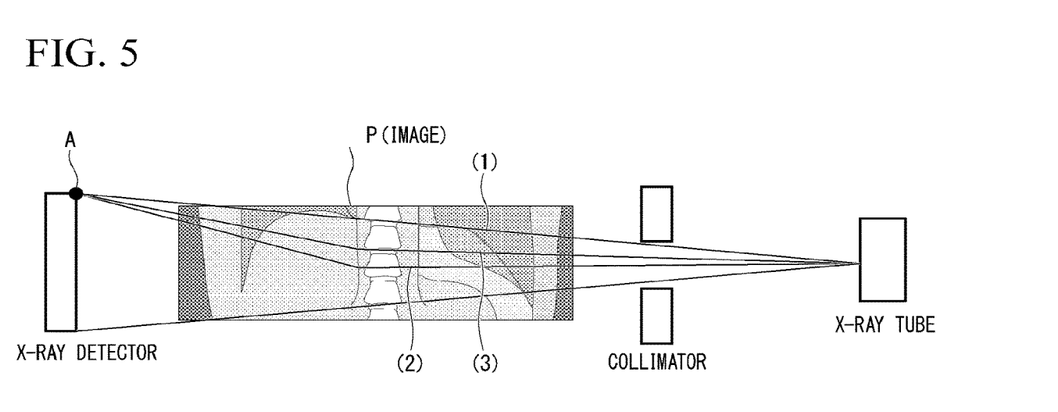
FIG. 5 is a diagram schematically showing a state in which scattered rays arrive at an optical sensor.

By acquiring the first projection data and the second projection data in this manner, the second projection data is less affected by scattered rays than the first projection data. This is because a relatively large amount of X rays in addition to X rays radiated to individual optical sensors pass through a scan target and thus there is a lot of opportunities for unintended scattered rays to arrive at optical sensors when the first projection data is acquired. FIG. 5 is a diagram schematically showing a state in which scattered rays arrive at an optical sensor. As shown in the figure, there are cases in which X rays (scattered rays) passing through paths (2) and (3) and the like in addition to X rays passing through an originally intended path (1) arrive at an optical sensor at a position A. Opportunities for these scattered rays to arrive at the optical sensor increase as the cone angle increases. Accordingly, the second projection data is less affected by scattered rays than the first projection data.

It is desirable to generate the machine learning model for each of scan conditions such as each view (each radiation angle), each radiation intensity represented as a tube voltage, each portion of a scan target, and the like. This is because a degree of occurrence of scattered rays changes when scan conditions change.

Figure 6:
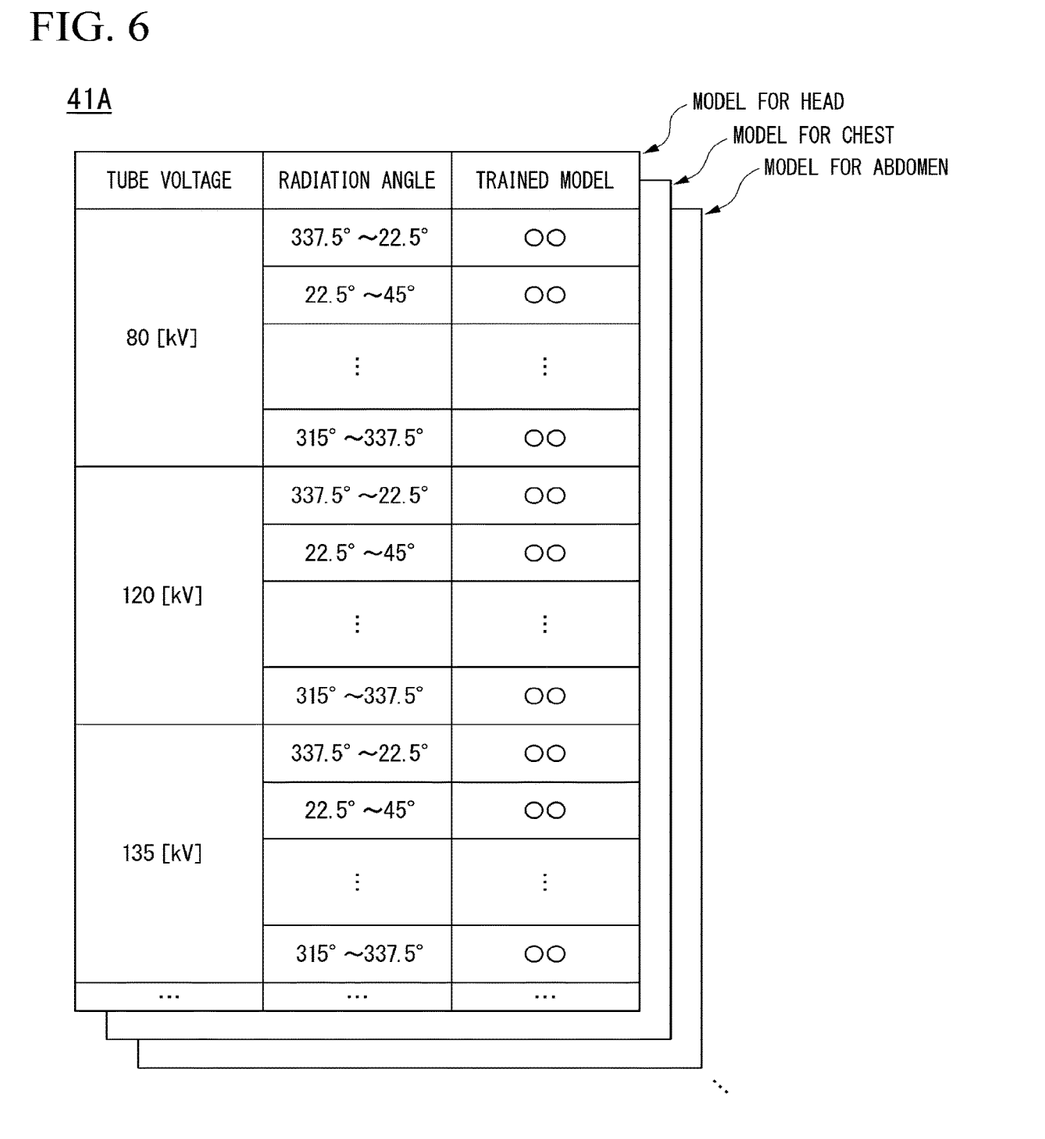
FIG. 6 is a diagram showing an example of a data configuration of a trained model.

A data structure and a program serving as a trained model may be stored as a trained model 41A in the memory 41 of the X-ray CT apparatus 1 at the time of sale of the X-ray CT apparatus 1 or installed as the trained model 41A in the memory 41 of the X-ray CT apparatus 1 after sale. In the latter case, the trained model 41A is transmitted to the X-ray CT apparatus 1 from the information processing apparatus 100 through the network NW, for example, and stored in the memory 41. In addition, the trained model 41A may be stored in a portable storage device and installed in the memory 41 as the trained model 41A by inserting the portable storage device into a drive device of the X-ray CT apparatus 1, which is not shown. [Utilization of trained model] Hereinafter, utilization of the trained model 41A by the preprocessing function 52 will be described. When the trained model 41A is prepared for each of scan conditions, a data configuration of the trained model 41A is as shown in FIG. 6. FIG. 6 is a diagram showing an example of a data configuration of the trained model 41A. As shown in the figure, the trained model 41A may be categorized into parts such as a model for the head, a model for the chest, and a model for the abdomen, for example, and each category includes trained models for each tube voltage and each radiation angle. The preprocessing function 52 reads a corresponding trained model from the memory 41 and uses the trained model on the basis of information on the examination subject P which is input prior to scanning.

Figure 7:
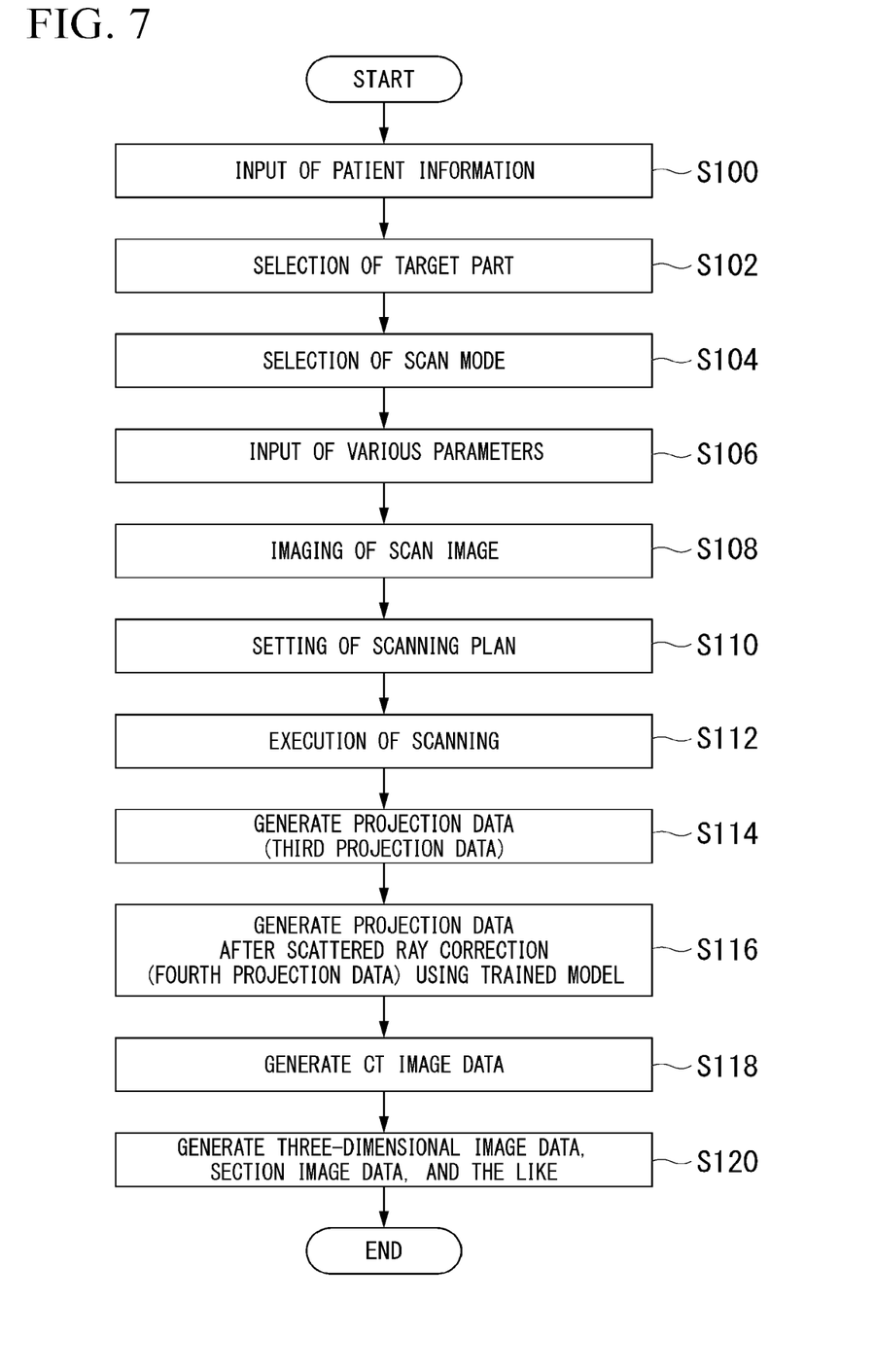
FIG. 7 is a flowchart showing an overview of processing performed in an X-ray CT apparatus according to an embodiment.

FIG. 7 is a flowchart showing an overview of processing performed in the X-ray CT apparatus 1 according to an embodiment. Meanwhile, with respect to processing presented in this flowchart, change, addition, deletion and the like of sequences can be appropriately performed.

First, the system control function 51 of the X-ray CT apparatus 1 receives patient information (information on the examination subject P) input to the input interface 43 while causing the display 42 to display an interface screen (step S100). Then, the system control function 51 receives selection of a target part through the input interface 43 (step S102). For example, graphic regions for selecting the target part are displayed on the display 42 and a user designates the target part by selecting any of the graphic regions. Thereafter, the system control function 51 receives selection of a scan mode through the input interface 43 (step S104). Then, the system control function 51 receives various parameters input to the input interface 43 (step S106). The various parameters include a tube voltage.

Next, the system control function 51 instructs the scan control function 55 to perform capturing of a scan image for positioning (step S108). The scan control function 55 instructs the X-ray high voltage device 14 and the control device 18 to image the examination subject P in two directions in a state in which the top board 33 is fixed, for example. The two directions may be the X direction and the Y direction in FIG. 1, for example.

Then, the system control function 51 receives a scanning plan setting input through the input interface 43 while causing the display 42 to display the scan image (step S110). For example, the system control function 51 receives setting of a scan position or setting input of a tilt angle of the gantry 10.

Then, the system control function 51 instructs the scan control function 55 to execute scanning (step S112).

When scanning is completed, the preprocessing function 52 generates projection data (third projection data) (step S114) and reads a trained model in accordance with scan conditions from the memory 41 (step S116). Then, the preprocessing function 52 generates projection data after scattered ray correction (fourth projection data) using the trained model (step S118). Thereafter, the reconstruction processing function 53 performs reconstruction processing to generate CT image data (step S120) and the image processing function 54 generates three-dimensional image data and section image data of an arbitrary section (step S122). Accordingly, processing of this flowchart ends.

According to the medical apparatus of the above-described first embodiment, it is possible to improve the definition of an image acquired by reconstructing the fourth projection data because the fourth projection data (projection data after scattered ray correction) is generated by inputting the third projection data collected by the X-ray CT apparatus 1 to a trained model which has been generated through learning using the first projection data collected by a first X-ray detector when a collimator provided in the first X-ray source included in a first scanner has a first opening width as learning data of an input side and using the second projection data collected by the first X-ray detector when the collimator provided in the first X-ray source has an opening width less than the first opening width as learning data of an output side.

Modified Example of First Embodiment

Although the trained model is generated using the second projection data acquired by narrowing a cone angle to be less than that for the first projection data as the learning data of the output side in the aforementioned embodiment, the present invention is not limited thereto and the second projection data may be projection data acquired by narrowing a fan angle to be less than that for the first projection data or projection data acquired by narrowing both the cone angle and the fan angle to be less than those for the first projection data.

Figure 8:
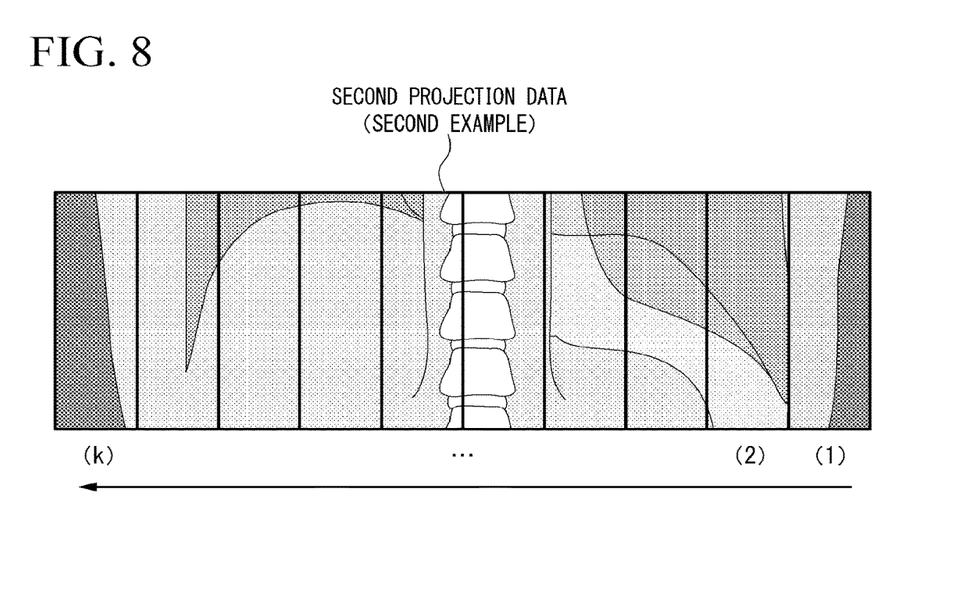
FIG. 8 is an image diagram showing a second example of second projection data acquired by narrowing a fan angle to be less than that of first projection data.

FIG. 8 is an image diagram showing a second example of the second projection data acquired by narrowing a fan angle to be less than that for the first projection data. The second projection data shown in FIG. 8 is acquired by narrowing an opening width, in the X-direction (refer to FIG. 2), of a collimator provided in the first X-ray source included in the first scanner to be less than that when the first projection data is acquired and radiating X rays in the order represented by parentheses in the figure, for example, while rotating the rotary frame 17.

Figure 9:
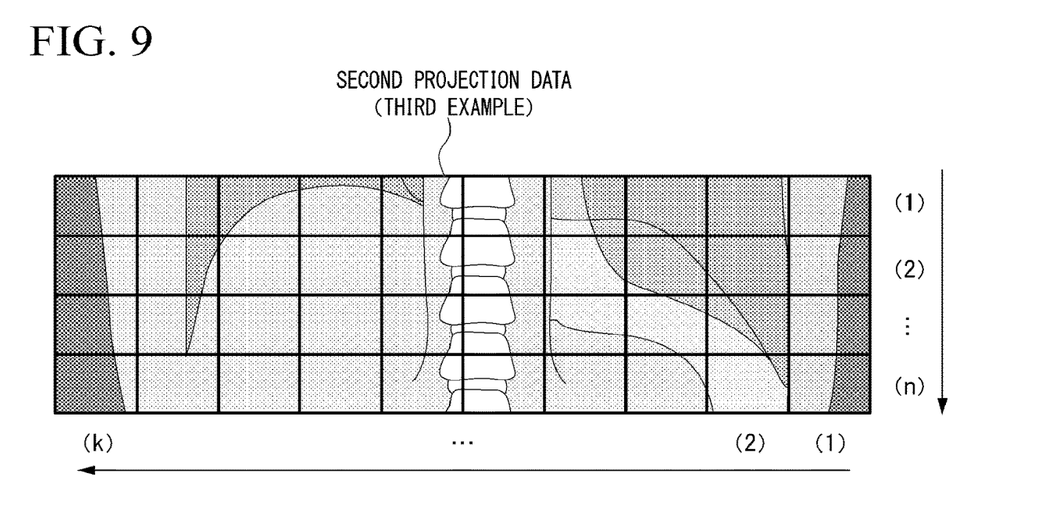
FIG. 9 is an image diagram showing a third example of second projection data acquired by narrowing both a cone angle and a fan angle to be less than those of first projection data.

FIG. 9 is an image diagram showing a third example of the second projection data acquired by narrowing both a cone angle and a fan angle to be less than those for the first projection data. The second projection data shown in FIG. 9 is acquired by narrowing an opening width, in the X-direction and the Z direction (refer to FIG. 2), of a collimator provided in the first X-ray source included in the first scanner to be less than those when the first projection data is acquired, rotating the X-ray tube n times while changing a radiation angle in the Z direction by changing an opening position of the collimator, and sequentially radiating X rays as in the example of FIG. 8 in each rotation. When the second projection data as shown in the example of FIG. 8 or FIG. 9 is used, the definition of an image obtained by reconstructing the fourth projection data acquired in the X-ray CT apparatus can also be improved in the same manner.

Second Embodiment

Hereinafter, a second embodiment will be described. A medical apparatus according to the second embodiment processes projection data collected by a multi-tube X-ray CT apparatus and generates projection data after scattered ray correction using a different trained model from that of the first embodiment. Although the entire X-ray CT apparatus according to the second embodiment is not shown, the X-ray CT apparatus according to the second embodiment is referred to as an X-ray CT apparatus 1A in the following.

Figure 10:
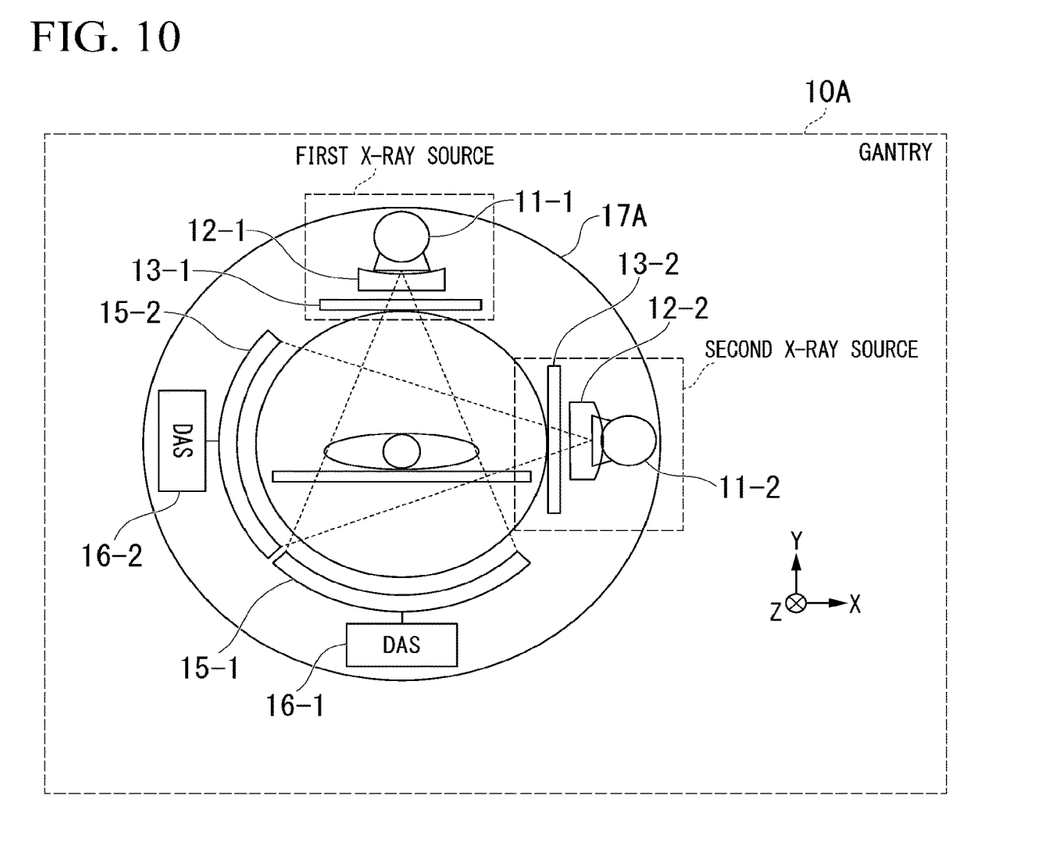
FIG. 10 is a diagram briefly showing a configuration of a gantry of an X-ray CT apparatus according to a second embodiment.

FIG. 10 is a diagram schematically showing a configuration of a gantry 10A of the X-ray CT apparatus 1A according to the second embodiment. The gantry 10A includes two combinations of an X-ray source including an X-ray tube 11, a wedge 12 and a collimator 13, and an X-ray detector 15 and a DAS 16 facing the X-ray source, for example. In the figure, symbols following hyphens represent components belonging to the respective combinations. In addition, there are cases in which the X-ray sources with respect to the respective combinations are referred to as a first X-ray source and a second X-ray source. Meanwhile, the X-ray CT apparatus 1A according to the second embodiment may include three or more combinations. In the example of FIG. 10, the first X-ray source and the second X-ray source are arranged such that radiation angles with respect to the examination subject P have a difference of 90° therebetween about the Z axis.

The X-ray CT apparatus 1A generates a CT image by combining projection data acquired by the first X-ray source, the X-ray detector 15-1 and the DAS 16-1 facing the X-ray source and projection data acquired by the second X-ray source, the X-ray detector 15-2 and the DAS 16-2 facing the second X-ray source in a state in which the first X-ray source and the second X-ray source have been controlled to simultaneously radiate X rays. For example, the X-ray CT apparatus 1A may generate a CT image by rotating the rotary frame 17 by 90° and combining projection data acquired by the first X-ray source and projection data acquired by the second X-ray source or radiate X rays through the first X-ray source and the second X-ray source by changing a tube voltage and generate a CT image on the basis of a difference image. Hereinafter, projection data acquired by controlling the first X-ray source and the second X-ray source such that they simultaneously radiate X rays is referred to as "projection data acquired in multi-tube state."

[Learning Processing]

Hereinafter, learning processing in the second embodiment will be described. In the second embodiment, a trained model is generated through learning using first projection data acquired in a multi-tube state as learning data of an input side and using second projection data acquired in a single-tube state as learning data of an output side. The single-tube state refers to a state in which X rays are radiated from only one X-ray source in an X-ray CT apparatus including a plurality of X-ray sources. When X rays are radiated in a multi-tube state, they are used for various purposes and are useful but X rays are radiated from positions different from a path through which X rays will arrive at a certain optical sensor. This inevitably increases opportunities for scattered rays to arrive at the optical sensor. In addition, since X rays are radiated from positions having a difference of 90° therebetween, there are cases in which it is impossible to sufficiently reduce the influence of scattered ray even when a collimator on the side of an X-ray source or a collimator on the side of an X-ray detector is used. In contrast, in learning processing of the second embodiment, a trained model generated through learning using the first projection data acquired in a multi-tube state as learning data of the input side and using the second projection data acquired in a single-tube state as learning data of the output side is used, and thus it is possible to improve the definition of an image obtained by reconstructing the fourth projection data acquired in the X-ray CT apparatus 1 as in the first embodiment.

Third Embodiment

Hereinafter, a third embodiment will be described. A medical apparatus according to the third embodiment generates projection data after scattered ray correction using a different trained model from that of the first embodiment.

[Learning Processing]

Figure 11:
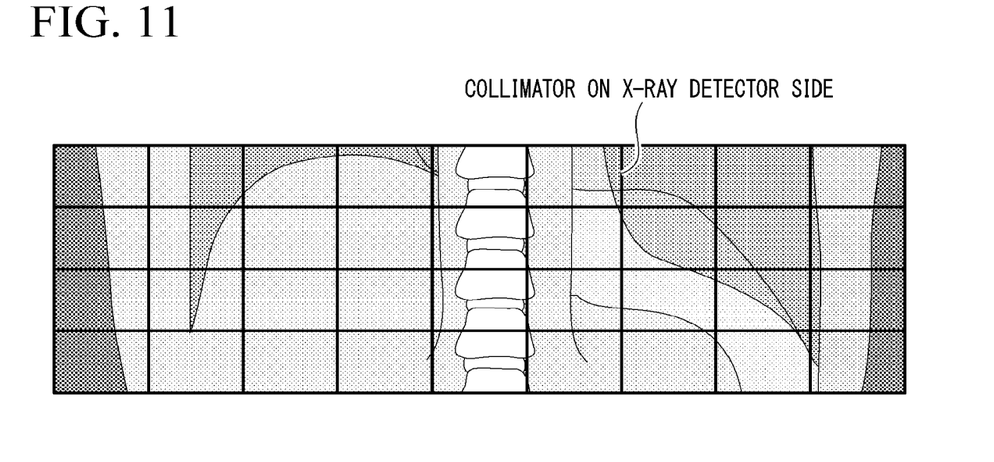
FIG. 11 is an image diagram showing an example of first projection data collected by an X-ray detector equipped with a first collimator.
Figure 12:
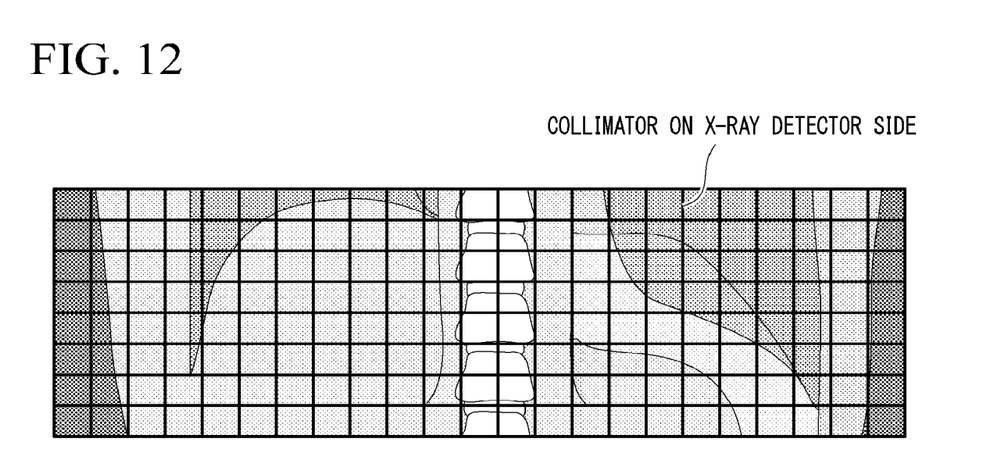
FIG. 12 is an image diagram showing an example of second projection data collected by an X-ray detector equipped with a second collimator.

Hereinafter, learning processing in the third embodiment will be described. In the third embodiment, a trained model is generated through learning using first projection data collected by a first X-ray detector when a first collimator is provided in the first X-ray detector as learning data of the input side and using second projection data collected by the first X-ray detector when a second collimator finer than the first collimator is provided in the first X-ray detector as learning data of the output side. That is, the first projection data is collected in an arbitrary X-ray CT apparatus in which the first collimator is disposed on the side of an X-ray detector and the second projection data is collected in a state in which the second collimator finer than the first collimator is provided in the X-ray CT apparatus. FIG. 11 is an image diagram showing an example of the first projection data collected by an X-ray detector having the first collimator provided therein and FIG. 12 is an image diagram showing an example of the second projection data collected by an X-ray detector having the second collimator provided therein.

By acquiring the first projection data and the second projection data in this manner, the second projection data is less affected by scattered rays than the first projection data. The same principle as that of the first embodiment is applied. According to the above-described third embodiment, since the first projection data is collected by the first X-ray detector when the first collimator is provided in the first X-ray detector and the second projection data is collected by the first X-ray detector when the second collimator finer than the first collimator is provided in the first X-ray detector, it is possible to improve the definition of an image obtained by reconstructing the fourth projection data acquired in the X-ray CT apparatus 1 as in the first embodiment.

Fourth Embodiment

Hereinafter, a fourth embodiment will be described. A medical apparatus according to the fourth embodiment generates projection data after scattered ray correction using a different trained model from that of the first embodiment.

[Learning Processing]

Hereinafter, learning processing in the fourth embodiment will be described. In the fourth embodiment, a trained model is generated through learning using a first projection data as learning data of the input side and using a second projection data as learning data of the output side. The first projection data includes at least two of projection data collected by a first X-ray detector when a first collimator is provided in the first X-ray detector, projection data collected by the first X-ray detector when a second collimator different from the first collimator is provided in the first X-ray detector, and projection data collected by the first X-ray detector when a collimator is not provided in the first X-ray detector. The second projection data includes projection data collected by the first X-ray detector when a third collimator finer than the first and second collimators is provided in the first X-ray detector.

Each of the three types of projection data included in the first projection data, i.e., each of the projection data collected by the first X-ray detector when the first collimator is provided in the first X-ray detector, the projection data collected by the first X-ray detector when the second collimator different from the first collimator is provided in the first X-ray detector, and the projection data collected by the first X-ray detector when the collimator is not provided in the first X-ray detector, is acquired by scanning a scan target while changing collection conditions of projection data of the X-ray detector 15 in the same X-ray CT apparatus 1.

The projection data included in the first projection data may be selected in any manner. For example, the information processing apparatus 100 may select, as the projection data included in the first projection data, at least two of the three types of projection data described above on the basis of an input operation received from an operator through the input interface 43. Alternatively, the information processing apparatus 100 may select, as the projection data included in the first projection data, predetermined at least two of the three types of projection data described above.

The second projection data is collected by the first X-ray detector, which is provided in the X-ray CT apparatus 1 used to acquire the first projection data, when the third collimator finer than the first and second collimators is provided in the first X-ray detector.

By acquiring the first projection data and the second projection data in this manner, the second projection data is less affected by scattered rays than the first projection data. The same principle as that of the first embodiment is applied.

According to the above-described fourth embodiment, since the first projection data includes at least two of projection data collected by the first X-ray detector when the first collimator is provided in the first X-ray detector, projection data collected by the first X-ray detector when the second collimator different from the first collimator is provided in the first X-ray detector, and projection data collected by the first X-ray detector when a collimator is not provided in the first X-ray detector, and the second projection data includes projection data collected by the first X-ray detector when the third collimator finer than the first and second collimators is provided in the first X-ray detector, it is possible to improve the definition of an image obtained by reconstructing the fourth projection data acquired in the X-ray CT apparatus 1 as in the first embodiment.

The above-described embodiments can be appropriately combined. For example, a trained model may be generated through learning using the first projection data collected when a collimator of an X-ray source has a first opening width in a multi-tube state as learning data of the input side and using the second projection data collected when a collimator of the X-ray source has a second opening width less than the first opening width in a single-tube state as learning data of the output side. Furthermore, for example, a trained model is generated through learning using, as learning data of the input side, first projection data collected by an X-ray detector when a collimator of an X-ray source has a first opening width and a collimator of the X-ray detector has a first fineness and using, as learning data of the output side, second projection data collected by the X-ray detector when the collimator of the X-ray source has a second opening width less than the first opening width and the collimator of the X-ray detector has a second fineness finer than the first fineness.

Modified Example of Each Embodiment

Although the type of the X-ray detector of the X-ray CT apparatus which acquires the first projection data and the second projection data is not particularly mentioned in the above-described embodiments, if the X-ray CT apparatus for acquiring the first projection data and the second projection data includes a double-layer detector, it is suitable because learning data having different tube voltages can be simultaneously collected.

Figure 13:
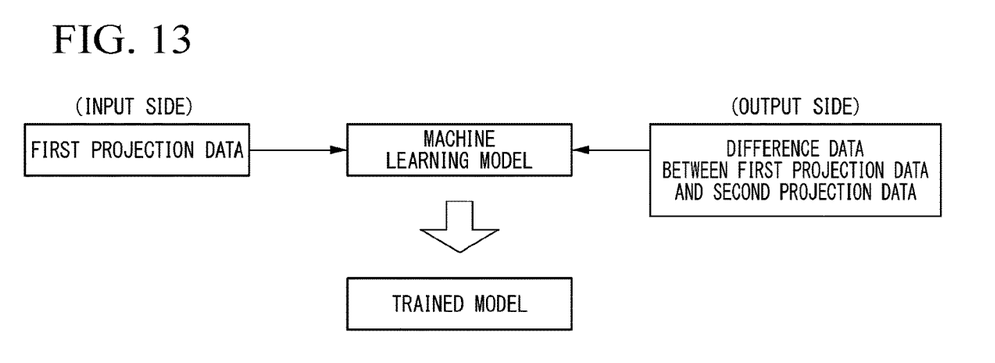
FIG. 13 is a diagram showing an overview of learning processing in a modified example.
Figure 14:
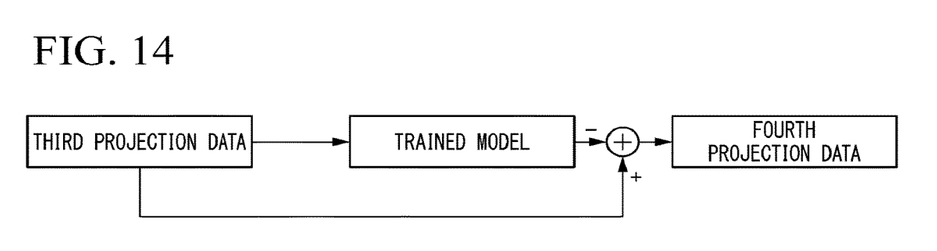
FIG. 14 is a diagram showing an overview of processing of generating fourth projection data in a modified example.

Although the fourth projection data is acquired by inputting the third projection data to the trained model in the above-described embodiments, the trained model generates scattered ray component data obtained by extracting the influence of scattered rays in projection data, and the pre-processing function 52 of the X-ray CT apparatus 1 may generate the fourth projection data by inputting the third projection data to the trained model and subtracting output data of the trained model from the third projection data. FIG. 13 is a diagram showing an overview of learning processing in a modified example and FIG. 14 is a diagram showing an overview of processing of generating the fourth projection data in the modified example. As shown in FIG. 13, the information processing apparatus 100 generates a trained model using the first projection data as learning data of the input side and using a difference between the first projection data and the second projection data as learning data of the output side. In addition, as shown in FIG. 14, the X-ray CT apparatus 1 generates the fourth projection data by inputting the third projection data to a trained model and subtracting the output of the trained model from the third projection data.

Furthermore, although projection data for which the influence of scattered rays has been reduced is acquired by inputting projection data to a trained model in the above-described embodiments, an image for which the influence of scattered rays is reduced may be acquired by inputting a reconstructed image to a trained model.

According to at least one of the above-described embodiments, it is possible to improve the definition of an image by including a processor which generates fourth projection data by inputting third projection data to a trained model which is generated through learning using first projection data collected by a first X-ray detector included in a first scanner and relatively greatly affected by scattered rays as learning data of an input side and using second projection data relatively less affected by scattered rays as learning data of an output side and generates the fourth projection data for which the influence of scattered rays in the third projection data has been reduced on the basis of the third projection data collected by a second X-ray detector included in a second scanner.

The above-described embodiments can be represented as follows.

A medical apparatus including:

a storage device storing a program and a trained model; and a hardware processor, wherein the trained model is generated through learning using first projection data collected by a first X-ray detector included in a first scanner and relatively greatly affected by scattered rays as learning data of an input side and using second projection data relatively less affected by scattered rays as learning data of an output side, and generates fourth projection data for which the influence of scattered rays in third projection data has been reduced on the basis of the third projection data collected by a second X-ray detector included in a second scanner, the hardware processor is configured to execute the program to input the third projection data to the trained model and to generate the fourth projection data, the first projection data is collected by the first X-ray detector in a case where a collimator provided in a first X-ray source included in the first scanner has a first opening width, and the second projection data is collected by the first X-ray detector in a case where the collimator is smaller than the first opening width.

Although several embodiments of the present invention have been described, these embodiments have been suggested as examples and are not intended to limit the scope of the invention. These embodiments can be implemented in other various forms and various omissions, substitutions and modifications are possible without departing from essential characteristics of the invention. These embodiments and modifications thereof are included in the scope and essential characteristics of the invention and also included in the invention disclosed in claims and the equivalents thereof.

What is claimed is:

1. A medical apparatus comprising processing circuitry configured to:
   input third projection data to a first trained model to generate fourth projection data, the first trained model being generated through learning using first projection data collected by a first X-ray detector included in a first scanner and relatively greatly affected by scattered rays as learning data of an input side and using second projection data relatively less affected by scattered rays as learning data of an output side, the first trained model being configured to generate, on the basis of the third projection data collected by a second X-ray detector included in a second scanner, the fourth projection data in which the influence of scattered rays in the third projection data has been reduced; or
   subtract, from the third projection data, scattered ray component data obtained by inputting the third projection data to a second trained model, to generate fifth projection data, the second trained model being generated through learning using the first projection data as learning data of an input side and using a difference between the first projection data and the second projection data as learning data of an output side, the second trained model being configured to generate, on the basis of the third projection data, the scattered ray component data obtained by extracting the influence of scattered rays in the third projection data,
   wherein
   the first projection data is collected by the first X-ray detector in a case where a collimator provided in a first X-ray source included in the first scanner has a first opening width, and
   the second projection data is collected by the first X-ray detector in a case where the collimator has an opening width smaller than the first opening width.

2. A medical apparatus comprising processing circuitry configured to:
   input third projection data to a first trained model to generate fourth projection data, the first trained model being generated through learning using first projection data collected by a first X-ray detector included in a first scanner and relatively greatly affected by scattered rays as learning data of an input side and using second projection data relatively less affected by scattered rays as learning data of an output side, the first trained model being configured to generate, on the basis of the third projection data collected by a second X-ray detector included in a second scanner, the fourth projection data in which the influence of scattered rays in the third projection data has been reduced; or
   subtract, from the third projection data, scattered ray component data obtained by inputting the third projection data to a second trained model, to generate fifth projection data, the second trained model being generated through learning using the first projection data as learning data of an input side and using a difference between the first projection data and the second projection data as learning data of an output side, the second trained model being configured to generate, on the basis of the third projection data, the scattered ray component data obtained by extracting the influence of scattered rays in the third projection data,
   wherein
   the first projection data is collected by the first X-ray detector in a case where a first collimator is provided in the first X-ray detector, and
   the second projection data is collected by the first X-ray detector in a case where a second collimator finer than the first collimator is provided in the first X-ray detector.

3. The medical apparatus according to claim 2, wherein
   the first projection data further includes at least one of projection data collected by the first X-ray detector in a case where a third collimator different from the first collimator is provided in the first X-ray detector and projection data collected by the first X-ray detector in a case where a collimator is not provided in the first X-ray detector, and
   the second projection data includes projection data collected by the first X-ray detector in a case where the second collimator finer than the first and third collimators is provided in the first X-ray detector.

4. A medical apparatus comprising processing circuitry configured to:
   input third projection data to a first trained model to generate fourth projection data, the first trained model being generated through learning using first projection data collected by a first X-ray detector included in a first scanner and relatively greatly affected by scattered rays as learning data of an input side and using second projection data relatively less affected by scattered rays as learning data of an output side, the first trained model being configured to generate, on the basis of the third projection data collected by a second X-ray detector included in a second scanner, the fourth projection data in which the influence of scattered rays in the third projection data has been reduced; or
   subtract, from the third projection data, scattered ray component data obtained by inputting the third projection data to a second trained model, to generate fifth projection data, the second trained model being generated through learning using the first projection data as learning data of an input side and using a difference between the first projection data and the second projection data as learning data of an output side, the second trained model being configured to generate, on the basis of the third projection data, the scattered ray component data obtained by extracting the influence of scattered rays in the third projection data,
   wherein
   the first projection data is collected by the first X-ray detector in a case where a plurality of X-ray sources included in the first scanner radiate X rays, and
   the second projection data is collected by the first X-ray detector in a case where any one of the plurality of X-ray sources radiates X rays.

5. The medical apparatus according to claim 4, wherein
   the second projection data is collected in a state in which a path of X rays is limited as compared to the first projection data.

* * * * *